(12) United States Patent
Schramm

(10) Patent No.: US 10,322,200 B2
(45) Date of Patent: Jun. 18, 2019

(54) CANDLE WARMING IMAGE DISPLAY LAMP

(71) Applicant: Michael R. Schramm, Perry, UT (US)

(72) Inventor: Michael R. Schramm, Perry, UT (US)

( * ) Notice: Subject to any disclaimer, the term of this patent is extended or adjusted under 35 U.S.C. 154(b) by 607 days.

(21) Appl. No.: 14/604,928

(22) Filed: Jan. 26, 2015

(65) Prior Publication Data

US 2015/0328353 A1    Nov. 19, 2015

Related U.S. Application Data

(60) Provisional application No. 61/931,576, filed on Jan. 25, 2014.

(51) Int. Cl.

| | |
|---|---|
| *A61L 9/02* | (2006.01) |
| *F21S 6/00* | (2006.01) |
| *F21V 33/00* | (2006.01) |
| *A47J 36/24* | (2006.01) |
| *F21S 9/02* | (2006.01) |
| *F21V 35/00* | (2006.01) |
| *A61L 9/03* | (2006.01) |
| *F21W 121/00* | (2006.01) |
| *F21W 131/30* | (2006.01) |

(52) U.S. Cl.
CPC .............. *A61L 9/02* (2013.01); *A47J 36/2477* (2013.01); *A47J 36/2494* (2013.01); *A61L 9/03* (2013.01); *F21S 6/00* (2013.01); *F21S 6/001* (2013.01); *F21S 9/02* (2013.01); *F21V 33/00* (2013.01); *F21V 33/0024* (2013.01); *F21V 33/0028* (2013.01); *F21V 33/0032* (2013.01); *F21V 35/00* (2013.01); *A61L 2209/12* (2013.01); *F21W 2121/00* (2013.01); *F21W 2131/30* (2013.01)

(58) Field of Classification Search
CPC .... A47J 36/2494; A47J 36/24; A47J 36/2477; F21V 33/0032; F21V 33/0024; F21V 33/00; F21V 33/0028; F21V 35/00; F21S 9/02; F21S 6/001; F21S 6/00; A61L 9/03; A61L 2/00; A61L 9/00; A61L 9/02; F21W 2131/30; F21W 2121/00
USPC .............................. 99/483; 362/183; 392/393
See application file for complete search history.

(56) References Cited

U.S. PATENT DOCUMENTS

| | | | | |
|---|---|---|---|---|
| 218,750 | A * | 8/1879 | Jory ........................ | G09F 13/06 40/580 |
| 676,924 | A * | 6/1901 | Steiger .................... | A61J 19/00 131/231 |
| 786,610 | A * | 4/1905 | Terrey ..................... | G09F 11/29 362/399 |
| 861,689 | A * | 7/1907 | Wilhems ................. | G09F 13/06 362/107 |
| 1,210,397 | A * | 1/1917 | Bang ....................... | A61J 19/00 131/236 |

(Continued)

OTHER PUBLICATIONS

Coo Candles LLC, Memory Box—2016 Coo Candle Website.
(Continued)

*Primary Examiner* — Eric S Stapleton
(74) *Attorney, Agent, or Firm* — Michael R. Schramm

(57) ABSTRACT

The present invention is a candle warming image display lamp (CWIDL) for use in displaying user selectable images while providing light such as to light a room brightly or as a night light, while also warming a preferably spill resistant wickless scented candle, without spilling hot molten candle wax.

20 Claims, 4 Drawing Sheets

(56) References Cited

U.S. PATENT DOCUMENTS

| | | | | |
|---|---|---|---|---|
| 1,254,714 A * | 1/1918 | McCombs | A45D 40/265 | 220/698 |
| 1,660,760 A * | 2/1928 | Murphy | A47G 33/00 | 362/806 |
| 1,764,639 A * | 6/1930 | Nathansohn | G09F 13/14 | 40/561 |
| 1,915,236 A * | 6/1933 | Lough | G09B 29/00 | 40/502 |
| 2,001,312 A * | 5/1935 | O'Connell | F21V 35/00 | 40/541 |
| 2,152,285 A * | 3/1939 | Schirmer | A24F 19/00 | 131/240.1 |
| 2,274,823 A * | 3/1942 | Candy, Jr. | C11C 5/008 | 264/263 |
| 2,298,940 A * | 10/1942 | Hayes | G09F 13/26 | 40/577 |
| 2,461,549 A * | 2/1949 | Hull | A24F 19/10 | 131/231 |
| 2,548,706 A * | 4/1951 | Corning | G09F 23/08 | 220/377 |
| 2,749,733 A * | 6/1956 | Smith | F23D 14/28 | 222/3 |
| 2,797,136 A * | 6/1957 | Nelson | B60N 3/083 | 131/231 |
| 2,810,491 A * | 10/1957 | Goldschmidt | B65D 25/02 | 15/257.074 |
| 2,858,639 A * | 11/1958 | Lawrence | A63H 33/28 | 446/16 |
| 2,945,314 A * | 7/1960 | Baldwin | A47G 19/2227 | 40/324 |
| 3,077,981 A * | 2/1963 | Gaspard | B42D 15/045 | 206/223 |
| 3,285,694 A * | 11/1966 | Marchi | A01M 1/2066 | 422/305 |
| 3,286,492 A * | 11/1966 | Frazier, Jr. | C11C 5/008 | 40/541 |
| 3,334,218 A * | 8/1967 | Nawrocki | F21L 21/00 | 362/161 |
| 3,342,363 A * | 9/1967 | Thrush | B65D 51/24 | 215/227 |
| 3,368,198 A * | 2/1968 | Eikenberry | G08G 1/095 | 340/815.54 |
| 3,374,911 A * | 3/1968 | White | A45D 40/0068 | 215/12.2 |
| 3,464,599 A * | 9/1969 | Meth | B43L 25/00 | 15/257.075 |
| 3,561,146 A * | 2/1971 | Dembar | A47G 1/14 | 40/661 |
| 3,579,898 A * | 5/1971 | Hein | A47K 5/122 | 446/16 |
| 3,596,391 A * | 8/1971 | Knight, Jr. | A63H 33/04 | 40/720 |
| 3,666,936 A * | 5/1972 | Webster, Jr. | G09F 13/10 | 362/812 |
| RE27,449 E * | 8/1972 | Bartz | B65B 3/26 | 141/1 |
| 3,703,045 A * | 11/1972 | Nyman | A47G 1/14 | 40/720 |
| 3,716,936 A * | 2/1973 | Miller | A47G 1/14 | 40/720 |
| 3,743,370 A * | 7/1973 | Lindsay | H04B 1/08 | 312/7.1 |
| 3,774,332 A * | 11/1973 | Schneider | G09F 1/12 | 40/720 |
| 3,781,164 A * | 12/1973 | McCaffery | F21V 35/00 | 220/659 |
| 3,818,627 A * | 6/1974 | Lebensfeld | A63H 33/28 | 215/365 |
| D233,295 S * | 10/1974 | Sandidge | F21V 35/00 | D6/683.1 |
| 3,840,678 A * | 10/1974 | Price | A21D 13/009 | 426/104 |
| 3,853,259 A * | 12/1974 | Tupper | B65D 5/48014 | 206/746 |
| 3,990,166 A * | 11/1976 | Nagelkirk | G09F 13/10 | 200/568 |
| 4,073,612 A * | 2/1978 | Nitta | F23Q 2/36 | 40/373 |
| 4,163,333 A * | 8/1979 | Kwiatkowski | F21V 35/00 | 362/161 |
| 4,180,938 A * | 1/1980 | La Fata | A63H 33/28 | 446/15 |
| 4,181,745 A * | 1/1980 | Growe | A23L 1/275 | 426/250 |
| 4,195,729 A * | 4/1980 | Macken | A47G 1/14 | 206/216 |
| 4,240,783 A * | 12/1980 | Nevin | A24F 15/08 | 431/126 |
| 4,301,841 A * | 11/1981 | Sandow | B65D 23/10 | 141/326 |
| 4,380,292 A * | 4/1983 | Cramer | A61M 5/3205 | 128/919 |
| 4,419,103 A * | 12/1983 | Balkan | B05C 11/08 | 118/18 |
| 4,438,564 A * | 3/1984 | Ashton | A47J 43/281 | 30/324 |
| 4,573,586 A * | 3/1986 | Helmer | B44D 3/04 | 206/563 |
| 4,619,373 A * | 10/1986 | Galer | B65D 43/0206 | 220/783 |
| 4,693,205 A * | 9/1987 | Thill | B44C 1/04 | 118/13 |
| 4,759,104 A * | 7/1988 | Buerosse | A61G 17/00 | 27/1 |
| 4,759,105 A * | 7/1988 | Buerosse | A61G 17/00 | 27/1 |
| 4,781,895 A * | 11/1988 | Spector | A01M 1/2088 | 261/DIG. 88 |
| 4,840,597 A * | 6/1989 | Perez | A63H 33/28 | 220/719 |
| 4,880,377 A * | 11/1989 | Ficho | F23Q 2/365 | 431/126 |
| 4,897,948 A * | 2/1990 | Owen | G09F 23/08 | 40/661 |
| 4,907,140 A * | 3/1990 | Overstreet | F21S 13/12 | 229/155 |
| 4,921,713 A * | 5/1990 | Fowler | A47G 21/183 | 239/33 |
| 4,928,412 A * | 5/1990 | Nishiyama | A47G 19/2227 | 40/324 |
| 4,930,235 A * | 6/1990 | Gillen | G09F 1/12 | 40/661 |
| 4,957,464 A * | 9/1990 | Perez | A63H 33/28 | 446/15 |
| 4,967,687 A * | 11/1990 | McShane | B05C 17/00 | 118/13 |
| 4,979,325 A * | 12/1990 | White | A47G 1/14 | 215/12.2 |
| 4,981,239 A * | 1/1991 | Cappel | B65D 47/40 | 222/109 |
| 4,984,714 A * | 1/1991 | Sledge | B65D 47/122 | 215/228 |
| 5,022,559 A * | 6/1991 | Condon | B65D 25/00 | 15/104.94 |
| 5,074,239 A * | 12/1991 | Law | B44D 3/00 | 118/26 |
| 5,088,950 A * | 2/1992 | LaFata | A46B 11/00 | 15/168 |
| 5,105,975 A * | 4/1992 | Patterson | A47G 19/2272 | 215/229 |
| 5,143,294 A * | 9/1992 | Lintvedt | B05B 7/2481 | 222/105 |
| 5,154,600 A * | 10/1992 | Sylvestre | B60Q 7/00 | 206/573 |
| 5,169,026 A * | 12/1992 | Patterson | B67B 7/28 | 220/703 |
| 5,178,451 A * | 1/1993 | Henry | F21V 35/00 | 206/216 |

(56) References Cited

U.S. PATENT DOCUMENTS

| | | | | |
|---|---|---|---|---|
| 5,226,252 A * | 7/1993 | Haluska | A44B 15/005 | 206/38.1 |
| 5,246,046 A * | 9/1993 | Schramm | B65D 23/00 | 141/311 A |
| 5,304,085 A * | 4/1994 | Novak | A63H 33/28 | 401/122 |
| 5,495,876 A * | 3/1996 | Schramm | B65D 23/00 | 141/339 |
| 5,511,685 A * | 4/1996 | Nelson | A47G 19/2227 | 220/662 |
| 5,553,735 A * | 9/1996 | Kimura | A47G 19/2227 | 220/62.18 |
| D378,622 S * | 3/1997 | Dimopoulos | F21V 35/00 | D27/144 |
| 5,613,764 A * | 3/1997 | O'Brien | F21S 8/00 | 362/307 |
| 5,647,052 A * | 7/1997 | Patel | A61L 9/03 | 392/390 |
| 5,651,669 A * | 7/1997 | Henry | A23G 3/28 | 248/910 |
| 5,651,942 A * | 7/1997 | Christensen | A61L 9/03 | 422/125 |
| 5,678,684 A * | 10/1997 | Wright | B44D 3/12 | 206/1.8 |
| 5,683,239 A * | 11/1997 | Cardosi | F23D 3/16 | 362/163 |
| D388,197 S * | 12/1997 | Cardosi | F21V 35/00 | D26/9 |
| D388,522 S * | 12/1997 | Pietrantoni | F21V 35/00 | D26/9 |
| 5,704,821 A * | 1/1998 | Mann | A63H 33/28 | 446/16 |
| 5,758,797 A * | 6/1998 | Martindale | B65D 25/00 | 220/719 |
| 5,787,838 A * | 8/1998 | Abrams | B65D 31/02 | 118/13 |
| 5,822,088 A * | 10/1998 | Danno | G03H 1/22 | 359/1 |
| D401,147 S * | 11/1998 | Miller | F21V 35/00 | D26/9 |
| 5,832,969 A * | 11/1998 | Schramm | B65D 23/00 | 141/311 A |
| D402,201 S * | 12/1998 | Miller | F21V 35/00 | D26/9 |
| RE36,131 E * | 3/1999 | Schramm | B65D 23/00 | 141/311 A |
| 5,894,948 A * | 4/1999 | Yeh | A47G 19/2227 | 215/12.1 |
| 5,895,679 A * | 4/1999 | Pender | A23L 1/275 | 118/13 |
| 5,908,057 A * | 6/1999 | Schramm | B65D 23/00 | 141/311 A |
| 6,008,172 A * | 12/1999 | Broshi | A23G 3/346 | 424/49 |
| 6,012,185 A * | 1/2000 | Woods | A47C 19/024 | 248/188.2 |
| 6,015,327 A * | 1/2000 | Kovacs | A63H 33/28 | 446/15 |
| 6,032,824 A * | 3/2000 | Barrow | A01K 5/0135 | 220/621 |
| 6,036,024 A * | 3/2000 | Seidler | B65D 71/0055 | 206/476 |
| 6,106,786 A * | 8/2000 | Akahoshi | A61L 9/122 | 222/187 |
| 6,135,842 A * | 10/2000 | LaFata | A63H 33/28 | 206/207 |
| 6,168,021 B1 * | 1/2001 | Herbruck | B65D 81/3294 | 206/521.8 |
| 6,186,853 B1 * | 2/2001 | Messina | A63H 33/28 | 446/15 |
| 6,216,856 B1 * | 4/2001 | Park | B43M 99/003 | 206/214 |
| 6,227,388 B1 * | 5/2001 | Borzelleca | E06B 7/28 | 211/1.3 |
| 6,234,786 B1 * | 5/2001 | Wagner | F21V 35/00 | 362/161 |
| 6,256,914 B1 * | 7/2001 | Yeh | A45C 1/12 | 40/711 |
| 6,315,433 B1 * | 11/2001 | Cavello | F21S 13/12 | 362/101 |
| 6,328,935 B1 * | 12/2001 | Buccellato | A61L 9/03 | 422/123 |
| 6,354,710 B1 * | 3/2002 | Nacouzi | F21S 13/12 | 219/220 |
| 6,361,752 B1 * | 3/2002 | Demarest | A61L 9/037 | 165/104.26 |
| 6,386,138 B1 * | 5/2002 | Schramm | B65D 23/00 | 118/13 |
| 6,399,027 B1 * | 6/2002 | Shah | A61L 9/12 | 422/1 |
| 6,413,476 B1 * | 7/2002 | Barnhart | A61L 9/03 | 422/123 |
| 6,422,859 B1 * | 7/2002 | Demetz | F23Q 2/36 | 40/454 |
| 6,461,014 B1 * | 10/2002 | Lin | F21S 10/002 | 362/101 |
| 6,474,980 B2 * | 11/2002 | LaVanier | F23D 3/16 | 431/126 |
| 6,488,494 B2 * | 12/2002 | Lee | F21V 35/00 | 40/451 |
| 6,491,516 B1 * | 12/2002 | Tal | A47G 33/00 | 273/147 |
| 6,520,822 B2 * | 2/2003 | Kennedy | A63H 33/28 | 446/15 |
| 6,530,815 B1 * | 3/2003 | Bro | A63H 15/06 | 446/15 |
| 6,533,117 B2 * | 3/2003 | Lundstrom | B65D 5/42 | 206/446 |
| 6,592,363 B2 * | 7/2003 | Hoffmann | F23D 3/26 | 126/45 |
| 6,595,822 B1 * | 7/2003 | Thai | A63H 33/28 | 446/16 |
| 6,619,811 B2 * | 9/2003 | Wang | A47G 19/2227 | 362/101 |
| 6,627,857 B1 * | 9/2003 | Tanner | A61L 9/03 | 219/445.1 |
| 6,629,870 B2 * | 10/2003 | Robinson | A63H 33/28 | 446/16 |
| 6,638,131 B1 * | 10/2003 | Thai | A63H 33/28 | 446/15 |
| 6,716,026 B1 * | 4/2004 | Beougher | F21V 35/00 | 431/290 |
| 6,717,789 B2 * | 4/2004 | Holman | G01D 3/032 | 307/105 |
| 6,733,548 B2 * | 5/2004 | Rasmussen | C11C 5/002 | 431/288 |
| 6,793,365 B1 * | 9/2004 | Rieck | A47G 33/06 | 362/161 |
| D502,101 S * | 2/2005 | Kerman | F21V 35/00 | D9/505 |
| 6,857,928 B2 * | 2/2005 | Thai | A63H 33/28 | 446/15 |
| 6,908,358 B2 * | 6/2005 | Lin | A63H 33/28 | 446/15 |
| 7,028,917 B2 * | 4/2006 | Buthier | A01M 1/2055 | 239/34 |
| D522,671 S * | 6/2006 | Niemeyer | F21V 35/00 | D26/20 |
| 7,067,772 B2 * | 6/2006 | Tanner | A61L 9/03 | 219/443.1 |
| 7,090,369 B1 * | 8/2006 | Jordan | F21V 35/00 | 362/170 |
| 7,132,084 B1 * | 11/2006 | Roumpos | A61L 9/02 | 126/110 C |
| 7,133,605 B2 * | 11/2006 | Niemeyer | A61L 9/03 | 219/438 |
| RE39,443 E * | 12/2006 | Schramm | B65D 23/00 | 141/311 A |

(56) References Cited

U.S. PATENT DOCUMENTS

| | | | | |
|---|---|---|---|---|
| 7,171,772 B1 * | 2/2007 | Male | G09F 13/04 | |
| | | | | 40/541 |
| 7,195,739 B1 * | 3/2007 | Penman | A61L 9/03 | |
| | | | | 219/236 |
| D542,431 S * | 5/2007 | Valentino | F21V 35/00 | |
| | | | | D26/11 |
| D542,432 S * | 5/2007 | Valentino | F21V 35/00 | |
| | | | | D26/11 |
| D542,433 S * | 5/2007 | Valentino | F21V 35/00 | |
| | | | | D26/11 |
| D542,437 S * | 5/2007 | Snow | F21V 35/00 | |
| | | | | D26/22 |
| 7,234,258 B2 * | 6/2007 | Nielson | G09F 3/18 | |
| | | | | 40/606.03 |
| 7,244,161 B2 * | 7/2007 | Thai | A63H 33/28 | |
| | | | | 215/388 |
| D550,033 S * | 9/2007 | Bodum | F21V 35/00 | |
| | | | | D7/509 |
| D550,034 S * | 9/2007 | Bodum | F21V 35/00 | |
| | | | | D7/509 |
| D551,502 S * | 9/2007 | Bodum | F21V 35/00 | |
| | | | | D7/509 |
| D556,511 S * | 12/2007 | Mansfield | F21V 35/00 | |
| | | | | D7/509 |
| 7,316,357 B2 * | 1/2008 | Lindahl | G06K 19/00 | |
| | | | | 235/380 |
| D562,074 S * | 2/2008 | Mansfield | F21V 35/00 | |
| | | | | D7/509 |
| 7,329,839 B2 * | 2/2008 | Palmer | F21V 35/00 | |
| | | | | 219/438 |
| 7,401,935 B2 * | 7/2008 | VanderSchuit | F21V 33/0028 | |
| | | | | 362/101 |
| D575,108 S * | 8/2008 | Barducci | F21V 35/00 | |
| | | | | D7/509 |
| D575,109 S * | 8/2008 | Barducci | F21V 35/00 | |
| | | | | D7/507 |
| D578,827 S * | 10/2008 | Barducci | F21V 35/00 | |
| | | | | D7/507 |
| 7,479,067 B2 * | 1/2009 | Gibson | A63B 57/357 | |
| | | | | 116/209 |
| 7,524,230 B2 * | 4/2009 | Thai | A63H 33/28 | |
| | | | | 446/15 |
| 7,548,684 B2 * | 6/2009 | Berrido | A61L 9/03 | |
| | | | | 392/390 |
| D596,461 S * | 7/2009 | Mansfield | F21V 35/00 | |
| | | | | D7/509 |
| 7,637,047 B1 * | 12/2009 | Nielson | G09F 3/18 | |
| | | | | 40/606.03 |
| D617,894 S * | 6/2010 | Wright | F21V 35/00 | |
| | | | | D24/121 |
| 7,815,263 B1 * | 10/2010 | Wright | F24B 1/02 | |
| | | | | 312/204 |
| D628,340 S * | 11/2010 | Krause | F21V 35/00 | |
| | | | | D26/128 |
| 7,942,109 B2 * | 5/2011 | Schramm | A63H 33/28 | |
| | | | | 118/13 |
| RE42,610 E * | 8/2011 | Schramm | F21V 35/00 | |
| | | | | 141/336 |
| D643,317 S * | 8/2011 | Clear | F21V 35/00 | |
| | | | | D10/46.3 |
| 8,113,343 B2 * | 2/2012 | Åkerlind | A24F 19/0085 | |
| | | | | 131/231 |
| 8,272,529 B2 * | 9/2012 | Mansfield | A47G 19/2205 | |
| | | | | 220/501 |
| D672,084 S * | 12/2012 | Ducey | F21V 35/00 | |
| | | | | D27/137 |
| 8,364,028 B1 * | 1/2013 | Vaske | A61L 9/03 | |
| | | | | 219/385 |
| 8,430,708 B1 * | 4/2013 | Schramm | A63H 33/28 | |
| | | | | 446/15 |
| D696,892 S * | 1/2014 | Bretillot | F21V 35/00 | |
| | | | | D23/366 |
| 8,693,852 B2 * | 4/2014 | Baraky | A61L 9/03 | |
| | | | | 392/386 |
| 8,765,073 B1 | 7/2014 | Hsiao | A61L 2/00 | |
| 8,800,188 B1 * | 8/2014 | Fishelis | A47B 43/006 | |
| | | | | 40/711 |
| 8,938,159 B2 | 1/2015 | Hsiao | 392/392 | |
| D723,676 S * | 3/2015 | Davis | F21V 35/00 | |
| | | | | D23/366 |
| 8,974,107 B2 | 3/2015 | Hsiao | 362/643 | |
| D725,909 S * | 4/2015 | Oxer | F21V 35/00 | |
| | | | | D3/304 |
| D729,371 S * | 5/2015 | Davis | F21V 35/00 | |
| | | | | D23/366 |
| 9,022,250 B2 * | 5/2015 | Stern | A47G 19/2205 | |
| | | | | 220/719 |
| 9,062,835 B2 * | 6/2015 | White | F21V 35/00 | |
| 9,109,780 B2 | 8/2015 | Hsiao | F21V 15/00 | |
| D739,615 S * | 9/2015 | Robertson | F21V 35/00 | |
| | | | | D30/129 |
| D742,561 S * | 11/2015 | Kasha | F21V 35/00 | |
| | | | | D26/22 |
| D742,562 S * | 11/2015 | Kasha | F21V 35/00 | |
| | | | | D26/22 |
| D742,563 S * | 11/2015 | Kasha | F21V 35/00 | |
| | | | | D26/22 |
| 9,181,023 B2 * | 11/2015 | Clinton | B65D 85/60 | |
| 9,186,000 B1 * | 11/2015 | Dominguez | A47G 1/0638 | |
| D746,108 S * | 12/2015 | Di Giuseppantonio | F21V 35/00 | |
| | | | | D7/509 |
| 9,271,589 B2 * | 3/2016 | Stern | A47G 19/2205 | |
| 9,314,708 B2 * | 4/2016 | Schramm | A63H 33/28 | |
| 9,498,553 B2 | 11/2016 | Hsiao et al. | A61L 9/03 | |
| 2001/0035413 A1 * | 11/2001 | Thai | A63H 33/28 | |
| | | | | 220/213 |
| 2002/0129763 A1 * | 9/2002 | Schramm | A63H 33/28 | |
| | | | | 118/13 |
| 2002/0132199 A1 * | 9/2002 | Lee | F21V 35/00 | |
| | | | | 431/153 |
| 2002/0133991 A1 * | 9/2002 | Nielson | G09F 3/18 | |
| | | | | 40/661 |
| 2002/0152672 A1 * | 10/2002 | Rasmussen | C11C 5/002 | |
| | | | | 44/275 |
| 2002/0185410 A1 * | 12/2002 | Travis-Pence | A47F 7/00 | |
| | | | | 206/736 |
| 2002/0187716 A1 * | 12/2002 | Kennedy | A63H 33/28 | |
| | | | | 446/15 |
| 2003/0007887 A1 * | 1/2003 | Roumpos | A61L 9/02 | |
| | | | | 422/1 |
| 2003/0086815 A1 * | 5/2003 | Wesley | A61L 9/037 | |
| | | | | 422/5 |
| 2003/0155364 A1 * | 8/2003 | Thai | A63H 33/28 | |
| | | | | 220/714 |
| 2004/0033067 A1 * | 2/2004 | He | A01M 1/2072 | |
| | | | | 392/395 |
| 2004/0084453 A1 * | 5/2004 | Thai | A63H 33/28 | |
| | | | | 220/259.1 |
| 2004/0250464 A1 * | 12/2004 | Rasmussen | C11C 5/002 | |
| | | | | 44/275 |
| 2005/0016985 A1 * | 1/2005 | Haas | A61L 9/03 | |
| | | | | 219/438 |
| 2005/0130552 A1 * | 6/2005 | Thai | A63H 33/28 | |
| | | | | 446/74 |
| 2005/0150886 A1 * | 7/2005 | Niemeyer | A61L 9/03 | |
| | | | | 219/385 |
| 2005/0163649 A1 * | 7/2005 | Friedrich | A61L 9/02 | |
| | | | | 422/1 |
| 2005/0188569 A1 * | 9/2005 | Derose | A47G 33/08 | |
| | | | | 40/544 |
| 2006/0006582 A1 * | 1/2006 | Strelnieks | B29C 67/241 | |
| | | | | 264/330 |
| 2006/0018786 A1 * | 1/2006 | Tolman | A61L 9/035 | |
| | | | | 422/5 |
| 2006/0163240 A1 * | 7/2006 | Xiao | A61L 9/03 | |
| | | | | 219/438 |

(56) References Cited

U.S. PATENT DOCUMENTS

| | | | | |
|---|---|---|---|---|
| 2006/0163241 A1* | 7/2006 | Xiao | A61L 9/03 | 219/438 |
| 2006/0227537 A1* | 10/2006 | Vanderschuit | F21V 33/0028 | 362/154 |
| 2006/0231718 A1* | 10/2006 | Calvanese | A47G 23/03 | 248/346.11 |
| 2006/0239870 A1* | 10/2006 | Schutte | A61L 9/03 | 422/125 |
| 2006/0240371 A1* | 10/2006 | Palmer | F21V 35/00 | 431/289 |
| 2007/0047931 A1* | 3/2007 | Niemeyer | A61L 9/03 | 392/390 |
| 2008/0272019 A1* | 11/2008 | Miller | B65D 81/365 | 206/457 |
| 2008/0273319 A1* | 11/2008 | VanderSchuit | A47G 19/2222 | 362/101 |
| 2008/0289975 A1* | 11/2008 | Sharber | A63H 33/28 | 206/207 |
| 2009/0323031 A1* | 12/2009 | Adler | F21S 13/12 | 353/62 |
| 2010/0270943 A1* | 10/2010 | Cook | A61L 9/03 | 315/291 |
| 2011/0014580 A1* | 1/2011 | Theresa | F23D 3/16 | 431/291 |
| 2014/0072286 A1 | 3/2014 | Hsiao et al. | A61L 9/03 | |
| 2014/0110389 A1 | 4/2014 | Hsiao | 219/385 | |
| 2014/0118992 A1 | 5/2014 | Hsiao | 392/96 | |
| 2014/0126181 A1 | 5/2014 | Hsiao | 392/96 | |
| 2014/0126891 A1 | 5/2014 | Hsiao | 392/393 | |
| 2014/0126892 A1 | 5/2014 | Hsiao | 392/394 | |
| 2014/0126893 A1 | 5/2014 | Hsiao | A61L 9/03 | |
| 2014/0161674 A1 | 6/2014 | Hsiao | A61L 9/03 | |
| 2014/0190858 A1* | 7/2014 | Schramm | A63H 37/00 | 206/457 |
| 2015/0328353 A1* | 11/2015 | Schramm | A61L 9/00 | 392/393 |

OTHER PUBLICATIONS

Cubee Co., Cubee—The Illuminating Photo Cube—2014 Cubee Website.

Serene House, NoSpill Wax Melt Warmer, Date = Unknown, Serene House Website.

Serene House, NoSpill Wax Melt Warmer, Date = Unknown, YouTube Website.

* cited by examiner

CANDLE WARMING IMAGE DISPLAY LAMP

CROSS REFERENCE TO RELATED APPLICATIONS

This U.S. nonprovisional utility patent application claims the benefit under 35 USC § 119(e) of U.S. provisional application No. 61/931,576 filed Jan. 25, 2014 which is incorporated in its entirety by this reference.

FIELD OF THE INVENTION

The present invention relates to light emitting lamps having changeable user selected images displayed thereon that simultaneously function as candle warmers, and more especially as wax spill resistant candle warmers.

BACKGROUND OF THE INVENTION

Lamps and night lights are well known in the art and have been widely used in providing light. Further image display apparatuses are well known in the art and have enjoyed considerable commercial success. Examples of such image display apparatuses are disclosed in U.S. Pat. Nos. 4,240,783, 7,234,258 and 7,637,047 and are expressly incorporated herein by reference. Further spill resistant containers having inwardly extending funnels are well known in the art and have enjoyed considerable commercial success. Examples of such spill resistant containers are disclosed in U.S. Pat. Nos. 5,246,046, 7,942,109, 8,430,708, and application 2014/0190858 and are expressly incorporated herein by reference. Further candle apparatuses are well known in the art and have enjoyed considerable commercial success. An example of such candle apparatuses is disclosed in U.S. Pat. No. 8,364,028, and is expressly incorporated herein by reference.

SUMMARY OF THE INVENTION

The present invention is a candle warming image display lamp (CWIDL) for use in displaying user selectable images while providing light such as to light a room brightly or as a night light, while also warming a preferably wickless scented candle, without spilling molten candle wax. The displayed images may be for instance printed photos. The lamp may be powered for instance by plugging the lamp into a power outlet or a USB port, or by batteries, or by a combination thereof. The candle is preferably a scented wickless candle comprising scented wax contained within an open container having a funnel extending therein. The candle is preferably adapted such that the candle may be readily positioned on top of the lamp such that the wax may be melted by heat from the lamp causing scent of the melted wax to waft from the candle into the room or other location where the lamp is located. The candle is preferably adapted such that when the candle is melted, and the candle is rotated in any orientation, molten candle wax will not run out of the candle. The candle is preferably adapted such that similar candles of various colors and scents may readily exchanged for the candle on top of the lamp.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
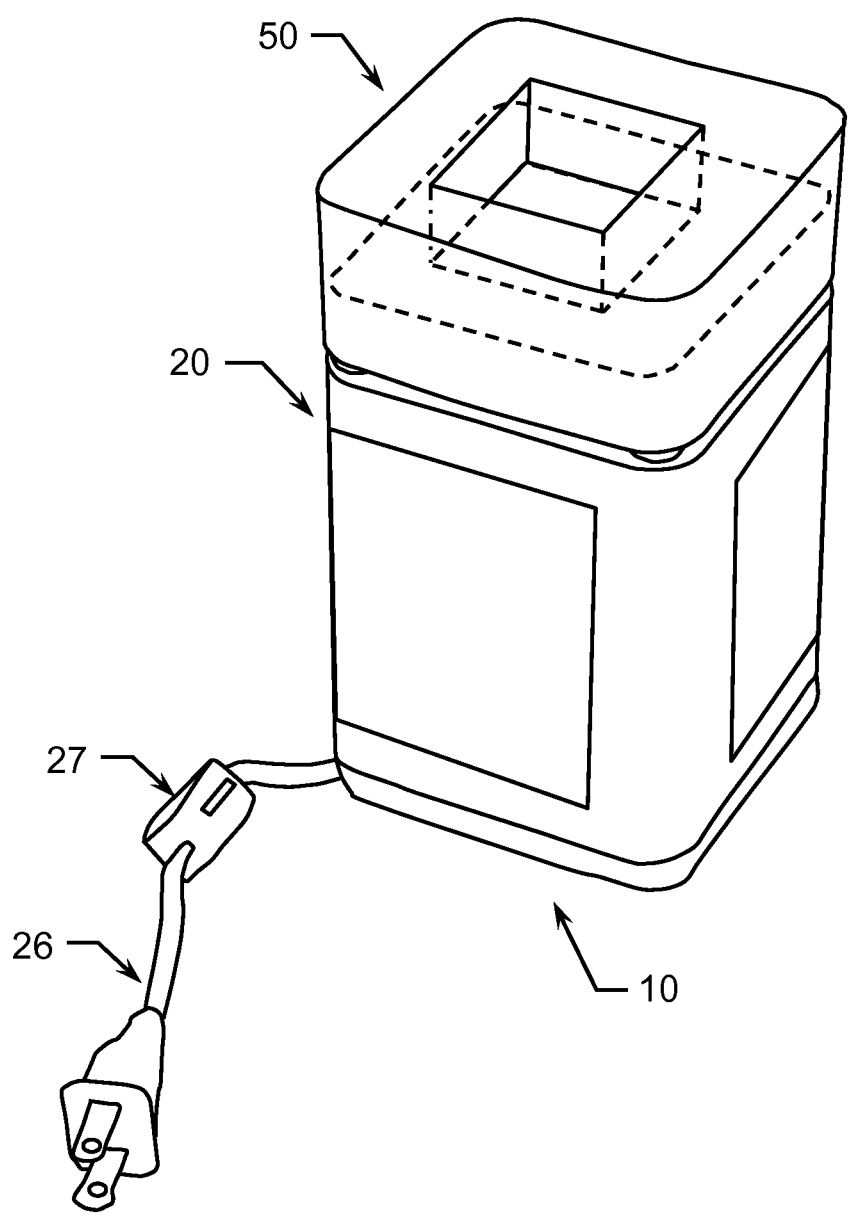
FIG. 1 is a trimetric view of the CWIDL in an assembled configuration.
Figure 2:
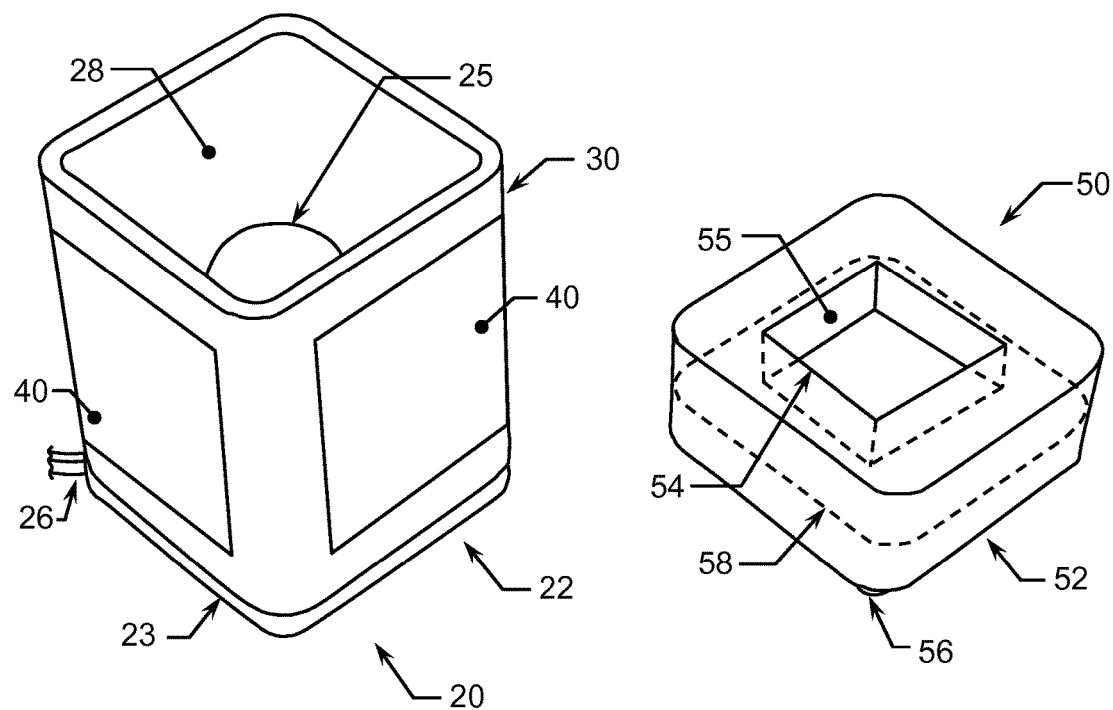
FIG. 2 is a trimetric view of the CWIDL in a partially disassembled configuration, with the candle assembly removed from the image display lamp.
Figure 3:
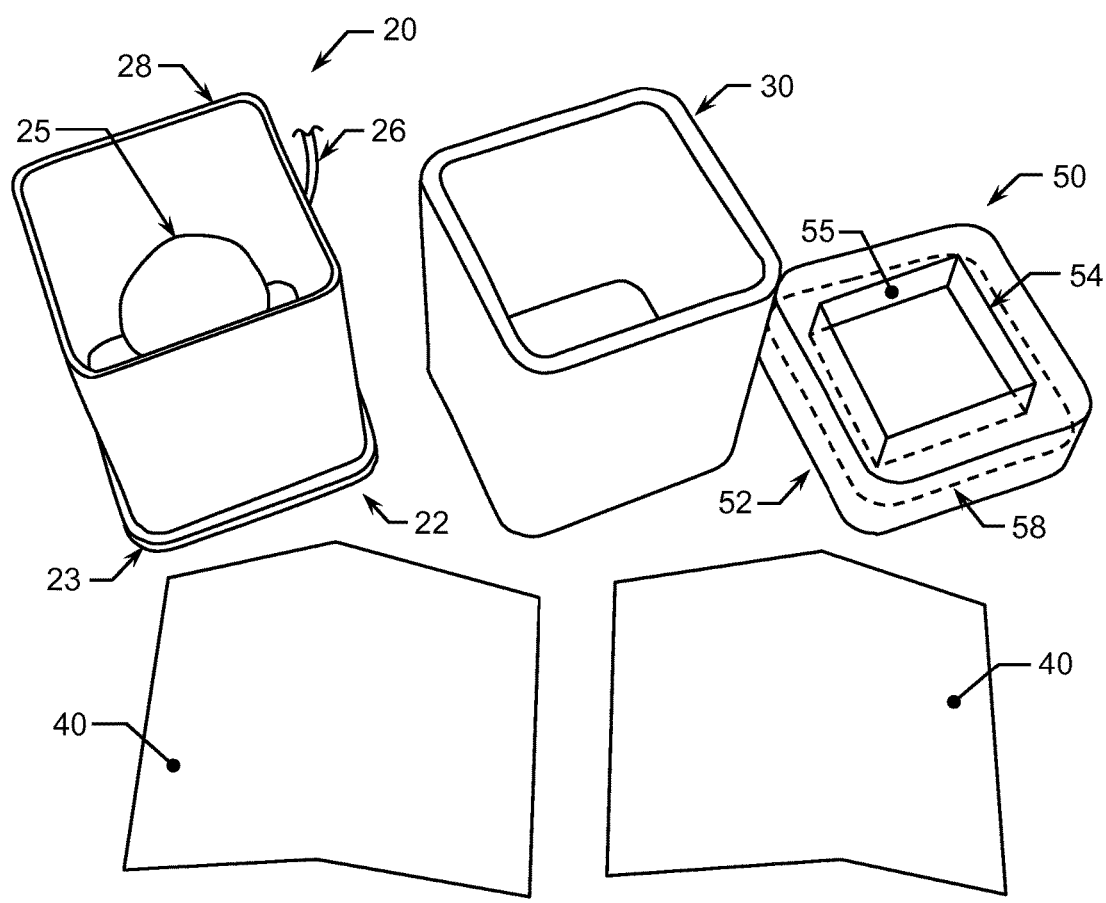
FIG. 3 is a trimetric view of the CWIDL in a disassembled configuration, with the candle assembly removed from the image display lamp, and with the image display lamp disassembled.
Figure 4:
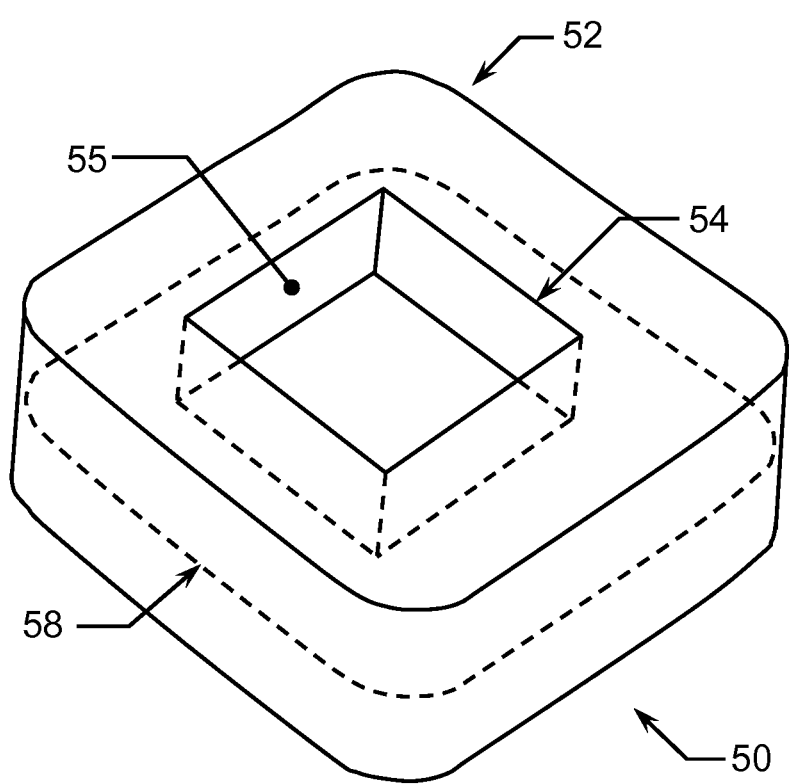
FIG. 4 is an enlarged trimetric view of the candle assembly.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

In order to facilitate the understanding of the present invention in reviewing the drawings accompanying the specification, a feature table is provided below. It is noted that like features are like numbered throughout all of the figures.

FEATURE TABLE

| #  | Feature                             | #  | Feature                  |
|----|-------------------------------------|----|--------------------------|
| 10 | Candle warming image display lamp apparatus | 20 | Image display lamp       |
| 22 | Base assembly                       | 23 | Base                     |
| 24 | Light bulb socket                   | 25 | Light bulb               |
| 26 | Electrical cord                     | 27 | Electrical switch        |
| 28 | Inner wall                          | 30 | Outer wall               |
| 40 | Display image                       | 50 | Candle assembly          |
| 52 | Container                           | 54 | Container upper opening  |
| 55 | Container funnel                    | 56 | Container feet           |
| 58 | Wax                                 |    |                          |

Referring now to the drawings, in a preferred embodiment the invention is a candle warming image display lamp apparatus 10 (CWIDL 10) for use in displaying user selectable images while providing light such as to light a room brightly or as a night light, while also warming a preferably wickless candle, without spilling molten candle wax comprising an image display lamp 20 and a candle assembly 50 removably mountable to the top of image display lamp 20. Image display lamp 20 further comprises a base assembly 22, an outer wall 30, and at least one display image 40. Base assembly 22 further comprises a base 23, a light bulb socket 24 (not shown) connected to base 23, a light bulb 25 electrically connected to light bulb socket 24, an electrical cord 26 electrically connected to light bulb socket 24, an electrical switch 27 electrically connected to electrical cord 26, and a preferably translucent inner wall 28 mounted to base 23. Image display lamp 20 further includes a preferably translucent outer wall 30 and at least one display image preferably defining an image printed on a paper or like substrate. Outer wall 30 is adapted to be slidingly positioned over inner wall 28 such that with the display image 40 may be displayably positioned in a gap formed between inner wall 28 and outer wall 30. Outer wall 30 preferably includes a flange on the top thereof that covers the gap formed between inner wall 28 and outer wall 30. It is noted that in an alternate embodiment, the image display lamp 20 may be powered by batteries or by a USB port mounted to base 23 or by batteries that are positioned within base 23 and recharged via a USB port that is mounted to base 23. Further, base 23 or other members of image display lamp 20 or candle assembly 50 may be made of glowing-in-the-dark or phosphorescent plastic. Candle assembly 50 further preferably defines a scented wickless candle assembly having a container 52 preferably defining generally translucent cubic shaped container having an upper opening 54 and a funnel 55 connected to upper opening 54 and extending inwardly into the inner cavity of container 52. Container 52 may include a plurality of feet 56 connect to an underside thereof. Container 52 may be a single integral structure or may be an assembly of structures such as a two piece container of a lower cup and an upper lid having a funnel such that the cup and lid fit together in a snap-tight configuration. Container 52 further includes a predetermined quantity of scented and preferably colored wax 58 cast into container 52. Container 52 may also optionally have a receiving flange to snappingly receive a snap-on cover for use when candle assembly 50 is not being heated or otherwise not in use such that scent of wax 58 is substantially contained within container 52 and such that wax 58 does not evaporate from candle assembly 50. Candle assembly 50 is adapted such that when wax 58 of candle assembly 50 is melted, because of inwardly extending funnel 55, wax 58 will not run out of container 52 regardless of the orientation in which the candle assembly 50 may be positioned. Candle assembly 50 is preferably adapted such that multiple instances of candle assembly 50 may be nestably stacked upon each other. It is noted that in an alternate embodiment, candle assembly 50 may have include wick.

In practice, with display image 40 positioned in image display lamp 20, image display lamp 20 electrically powered, and candle assembly 50 mounted upon display lamp 20, CWIDL 10 provides light while displaying a selected display image 40 and while spill resistantly warming candle assembly 50 without the use of a flame so as to cause the aroma of candle assembly 50 to waft from candle assembly 50 via container opening 54. CWIDL 10 may be adapted such that there is some gap between display lamp 20 and candle assembly 50 to allow for ventilation or air to pass therebetween. If the user desires to change display image 40, the user may merely remove candle assembly 50 from the display lamp 20, slide outer wall 30 off of inner wall 28, exchange display image 40 with a different image, replace outer wall 30, and replace candle assembly 50. If the user tires of the scent or color of candle assembly 50, or when wax 58 of candle assembly 50 is consumed, the user merely substitutes one instance of candle assembly 50 with another instance of candle assembly 50. Candle assembly 50 is preferably a disposable candle (i.e. candle assembly 50 is discarded after consumption of wax 58 of candle assembly 50), but may alternately be a serviceable candle (i.e. candle assembly 50 may be recycled by adding wax 58 to container 52 to replace consumed wax 58 or by adding additional fragrance to existing wax 58 to replace dispersed fragrance). It is further noted that the CWIDL 10 may optionally have a battery powered fan mounted thereon to aid in the dispersal of the scent of the candle.

In a first alternate embodiment, the invention is substantially identical to CWIDL 10 except that rather than using a light bulb to melt wax, the invention includes a heating element—such as those found in coffee cup warmers or wax warmers—to melt wax 58.

In a second alternate embodiment, the invention forms a fondue warming apparatus which is substantially identical to CWIDL 10 except that in the alternate embodiment, wax 58 of candle assembly 50 is replaced with chocolate, caramel, fudge, marsh mellows, or like edible composition having a relatively low melt temperature such that strawberries, pineapple fruit, marshmallows, and like edible snacks may be dipped into the melted composition and consumed as a fondue style treat.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A candle apparatus comprising at least one of a first container having an inner cavity and an open funnel extending into said inner cavity, and a quantity of meltable wax contained within said first container, wherein said quantity of meltable wax is such that when said quantity of meltable wax is melted and said first container is oriented in any orientation, said melted quantity of meltable wax will not run out of said first container, and a second container having an inner cavity and an open funnel extending into said inner cavity, and a quantity of meltable wax contained within said second container, wherein said apparatus is expressly adapted to mount to a heating apparatus.

2. The candle apparatus of claim 1, wherein said containers define plastic containers.

3. The candle apparatus of claim 1, wherein said candle apparatus defines at least one of a colored candle apparatus, a wickless candle apparatus, a scented candle apparatus, and a combination thereof.

4. The candle apparatus of claim 1, wherein said candle apparatus defines at least one of a disposable candle apparatus and a serviceable candle apparatus.

5. The candle apparatus of claim 1, wherein said candle apparatus defines at least one of a single member container and a container comprised of a plurality of discrete members joined to form said container.

6. The candle apparatus of claim 1, wherein said candle apparatus defines at least one of a candle apparatus adapted to nest with and stack upon another instance of said candle apparatus and a candle apparatus having a lid receiving member and being adapted to substantially hermetically engage a lid.

7. The candle apparatus of claim 1, wherein said candle apparatus is mounted on a heating apparatus.

8. The candle apparatus of claim 7, wherein said heating apparatus defines at least one of a heating element heating apparatus and a light-emitting heating apparatus.

9. The candle apparatus of claim 8, wherein said heating element heating apparatus further defines a heating apparatus expressly adapted to receive a candle apparatus at least partially within said heating element heating apparatus and to heat said candle apparatus such that said wax is melted and such that fragrance is emitted from an open funnel of said apparatus and yet such that if said candle apparatus is rotated or reoriented said melted wax will not run out of an open funnel of said apparatus and wherein said light-emitting heating apparatus further defines a lamp having a user selectable and modifiable image displayed thereon and expressly adapted to receive a candle apparatus at least partially within said light-emitting heating apparatus and to heat said candle apparatus such that said wax is melted and such that fragrance is emitted from an open funnel of said apparatus and yet such that if said candle apparatus is rotated or reoriented said melted wax will not run out of an open funnel of said apparatus.

10. A candle apparatus comprising at least one of a first open container having an inner cavity and a quantity of meltable wax contained therein, wherein said apparatus is adapted such that when said quantity of meltable wax is melted and said first container is oriented in any orientation, said melted quantity of meltable wax will not run out of said first container, and a second open container having an inner cavity and a quantity of meltable wax contained therein, wherein said apparatus is adapted such that when at least a portion of said quantity of meltable wax is melted and said second container is oriented in any orientation, said melted wax will not run out of said second container, and wherein said apparatus is expressly adapted to mount to a heating apparatus.

11. The candle apparatus of claim 10, wherein said containers include an open funnel extending into said inner cavities.

12. The candle apparatus of claim 10, wherein said candle apparatus defines at least one of a colored candle apparatus, a wickless candle apparatus, a scented candle apparatus, and a combination thereof.

13. The candle apparatus of claim 10, wherein said candle apparatus defines at least one of a disposable candle apparatus and a serviceable candle apparatus.

14. The candle apparatus of claim 10, wherein said candle apparatus defines at least one of a single member container and a container comprised of a plurality of discrete members joined to form said container.

15. The candle apparatus of claim 10, wherein said candle apparatus defines at least one of a candle apparatus adapted to nest with and stack upon another instance of said candle apparatus and a candle apparatus having a lid receiving member and being adapted to substantially hermetically engage a lid.

16. The candle apparatus of claim 10, wherein said candle apparatus is mounted on a heating apparatus.

17. The candle apparatus of claim 16, wherein said heating apparatus defines at least one of a heating element heating apparatus and a light-emitting heating apparatus.

18. The candle apparatus of claim 17, wherein said heating element heating apparatus further defines a heating apparatus expressly adapted to receive a candle apparatus at least partially within said heating element heating apparatus and to heat said candle apparatus such that said wax is melted and such that fragrance is emitted from an open container of said apparatus and yet such that if said candle apparatus is rotated or reoriented said melted wax will not run out of an open container of said apparatus and wherein said light-emitting heating apparatus further defines a lamp having a user selectable and modifiable image displayed thereon and expressly adapted to receive a candle apparatus at least partially within said light-emitting heating apparatus and to heat said candle apparatus such that said wax is melted and such that fragrance is emitted from an open container of said apparatus and yet such that if said candle apparatus is rotated or reoriented said melted wax will not run out of an open container of said apparatus.

19. A candle apparatus expressly adapted to be removably mounted to a heating apparatus and comprising at least one apparatus of a first container having an inner cavity and an open funnel extending into said inner cavity, and a quantity of meltable wax contained within said first container, and a second open container having an inner cavity and a quantity of meltable wax contained therein, wherein said apparatus is adapted such that when at least a portion of said wax is melted and said second container is oriented in any orientation, said melted wax will not run out of said second container.

20. The candle apparatus of claim 19, wherein said candle apparatus is mounted on at least one of a heating element heating apparatus and a light-emitting heating apparatus, and wherein said heating element heating apparatus further defines a heating apparatus expressly adapted to receive a candle apparatus at least partially within said heating element heating apparatus and to heat said candle apparatus such that said wax is melted and such that fragrance is emitted from a container of said apparatus and yet such that if said candle apparatus is rotated or reoriented said melted wax will not run out of a container of said apparatus and wherein said light-emitting heating apparatus further defines a lamp having a user selectable and modifiable image displayed thereon and expressly adapted to receive a candle apparatus at least partially within said light-emitting heating apparatus and to heat said candle apparatus such that said wax is melted and such that fragrance is emitted from a container of said apparatus and yet such that if said candle apparatus is rotated or reoriented said melted wax will not run out of a container of said apparatus.

\* \* \* \* \*